(12) United States Patent
Schwartz et al.

(10) Patent No.: US 7,914,703 B2
(45) Date of Patent: Mar. 29, 2011

(54) POLY(OXYALKYLENE)ATED COLORANTS AND THEIR USE AS FLUORESCENT SECURITY TAGGANTS

(75) Inventors: Russell Schwartz, Cincinnati, OH (US); Don DeRussy, Mason, OH (US); Daniel F. Gloster, San Diego, CA (US); Stephen Postle, Glen Rock, NJ (US); Rakesh Vig, Durham, CT (US); Ewell Cook, Middletown, NJ (US); Tatiana Romanova, Loveland, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 610 days.

(21) Appl. No.: 11/947,440

(22) Filed: Nov. 29, 2007

(65) Prior Publication Data
US 2008/0178763 A1    Jul. 31, 2008

Related U.S. Application Data

(60) Provisional application No. 60/867,660, filed on Nov. 29, 2006.

(51) Int. Cl.
*C08G 65/32* (2006.01)
*C08G 65/325* (2006.01)
*C07D 471/06* (2006.01)

(52) U.S. Cl. ......... 252/301.26; 252/301.16; 252/301.35; 252/965; 546/37; 428/690; 250/473.1; 106/31.64; 106/31.77

(58) Field of Classification Search ............. 252/301.26, 252/301.16, 301.35, 965; 546/37; 428/690; 250/473.1; 106/31.64, 31.77
See application file for complete search history.

(56) References Cited

U.S. PATENT DOCUMENTS

| | | | |
|---|---|---|---|
| 4,587,206 | A | 5/1986 | Sakaguchi et al. |
| 5,009,702 | A | 4/1991 | Keil et al. |
| 5,149,800 | A | 9/1992 | Kluger et al. |
| 5,177,200 | A | 1/1993 | Kluger et al. |
| 5,240,464 | A | 8/1993 | Kluger et al. |
| 5,270,363 | A | 12/1993 | Kluger et al. |
| 5,591,833 | A | 1/1997 | Hines et al. |
| 5,766,268 | A | 6/1998 | Bruhnke |
| 5,773,592 | A | 6/1998 | Mills |
| 5,935,272 | A | 8/1999 | Mahaffey et al. |
| 5,973,064 | A | 10/1999 | Zhao et al. |
| 5,998,621 | A | 12/1999 | Mahaffey |
| 6,498,945 | B1 | 12/2002 | Alfheim et al. |
| 6,806,368 | B2 | 10/2004 | Wurthner et al. |
| 2005/0054852 | A1 | 3/2005 | Fujita et al. |
| 2006/0020141 | A1 | 1/2006 | Banning et al. |
| 2006/0083890 | A1 | 4/2006 | Takizawa |

OTHER PUBLICATIONS

International Search Report and Written Opinion of International Searching Authority issued for the corresponding PCT International Application No. PCT/US2007/085901, May 19, 2008.

*Primary Examiner* — C. Melissa Koslow
(74) *Attorney, Agent, or Firm* — Kramer Levin Naftalis & Frankel LLP

(57) ABSTRACT

Certain poly(oxyalkylene) colorants are disclosed along with method of preparation thereof. A method of using these colorants as fluorescent security taggants is also disclosed.

12 Claims, 1 Drawing Sheet

POLY(OXYALKYLENE)ATED COLORANTS AND THEIR USE AS FLUORESCENT SECURITY TAGGANTS

FIELD OF THE INVENTION

The invention relates to specific poly(oxyalkylene) colorants and methods of preparation thereof. The invention also relates to the use of these colorants as fluorescent security taggants.

BACKGROUND OF THE INVENTION

Poly(oxyalkylene) polymeric colorants have been utilized to permanently color myriad substrates, including thermoplastic resins, such as disclosed in U.S. Pat. Nos. 4,284,729, 4,507,407, and 4,751,254; polyurethane foams, such as disclosed in U.S. Pat. No. 4,846,846; aqueous and non-aqueous liquids, such as disclosed in U.S. Pat. No. 4,871,371; and have been used as fugitive tints for textiles and threads, such as disclosed in U.S. Pat. No. 4,167,510. Such colorants provide effective and stable colorations to such materials, are easily handled, and exhibit desirable migratory properties within certain substrates.

3,4,9,10-Perylene tetracarboxylic acid bisimide based colorants are well known in industry and academia due to their favorable combination of light fastness, weather and thermal stability, as well as migration resistance in a number of applications such as coatings and plastics and inks. For this reason, they have been used extensively in the especially demanding applications of the automotive industry. These materials are insoluble pigments.

Patents DE 1130099 and GB 967178 first disclosed the potential for using perylenes as fluorescent dyes with high fluorescence quantum yield and photostability. However, these materials were only slightly soluble in organic solvents. An improvement in solubility was demonstrated by Langhals, et al, in *Heterocycles*, 1995, 40, 477 and references cited therein. Langhals reported that certain solubilizing substituents attached at the imide nitrogen such as long chain secondary alkyl groups (swallow-tail substituents) and 2,5-di tert-butylbenzene can enhance the solubility of perylene bisimdes in common organic solvents. These perylene bisimide dyes exhibit intense yellow fluorescence in solution with a quantum yield near unity. Even with the above-enhanced solubilizing groups, however, the materials are only soluble in common organic solvents at low concentrations. More recent applications for perylene bisimide dyes include dye laser applications, n-type semiconductors, and electrophotography.

Poly(oxyalkylene) substituents attached to organic chromophors have been used to make various colorants with enhanced dispersability and/or solubility, as disclosed in U.S. Pat. Nos. 4,141,684, 5,149,800, 5,177,200, 5,240,464, 5,270,363, 5,591,833, 5,766,268, 5,935,272, 5,973,064, 5,998,621 and the references cited therein. Applications reported thus far do not include the use of poly(oxyalkylene)ated chromophoric materials, especially perylene based materials, as fluorescent security taggants.

SUMMARY OF THE INVENTION

The present invention provides a perylene poly(oxyalkyle-ne)bisamide compound having the following chemical formula I:

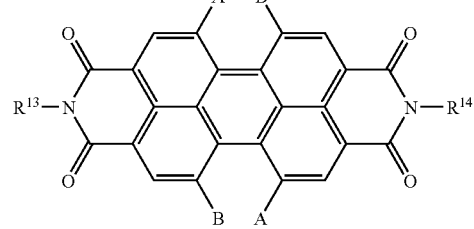

wherein each of A and B is independently selected from the group consisting of: H, OH, $OR^4$, $N(R^3)_2$, alkyl, F, Cl, Br, I, $NO_2$, CN, $^-NCS$, $^-SCN$; $R^3$ is selected from the group consisting of: alkyl, aralkyl, alkaryl, polyalkylene oxide; and each of $R^{13}$ and $R^{14}$ is independently a polyalkylene oxide. The present invention also provides the perylene compound of formula I, wherein each of A and B is H; and each of $R^{13}$ and $R^{14}$ comprises $(C_aH_{2a}O)_m(C_bH_{2b})_nCH_3$, where a and b are different and either 2 or 3, m is at least 3, and n is 1-31.

The present invention also provides a perylene poly(oxyalkylene) tetraamide compound having the following chemical formula II:

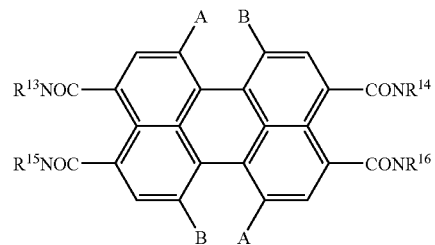

wherein each of A and B is independently selected from the group consisting of: H, OH, $OR^4$, $N(R^3)_2$, alkyl, F, Cl, Br, I, $NO_2$, CN, $^-NCS$, $^-SCN$; $R^3$ is selected from the group consisting of: alkyl, aralkyl, alkaryl, polyalkylene oxide; and each of $R^{13}$, $R^{14}$, $R^{15}$ and $R^{16}$ is independently a polyalkylene oxide.

The present invention further provides a triarylmethane compound having one of the following chemical formulae III or IV:

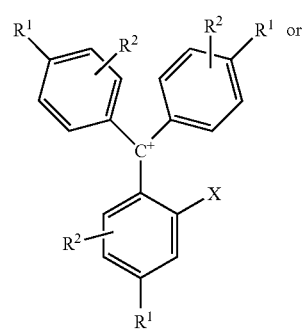

-continued

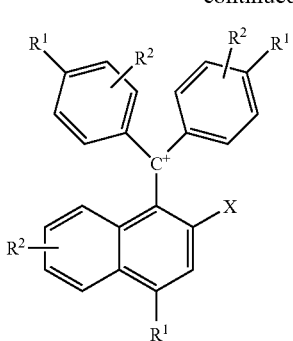

IV wherein X is H or $CO_2^-$ or $CO_2H$ [with a counterion $Z^-$]; $R^1$ is selected from the group consisting of H, $NR^3_2$, $OR^4$, alkyl, aryl and substituted aryl; $R^2$ is selected from the group consisting of H, $SO_3H$, $SO_3^-(1/n)M^{n+}$, $CO_2H$ and $CO_2$-$(1/n)$ $M^{n+}$; each of $R^3$, $R^4$ is independently selected from the group consisting of alkyl, aralkyl, alkaryl and polyalkylene oxide; Z is selected from the group consisting of halide, tosylate, brosylate, carboxylate, sulphate and phosphate; M is a cation; and n is integer from 1 to 4.

The present invention further provides a xanthene or thioxanthene compound having one of the following chemical formula V:

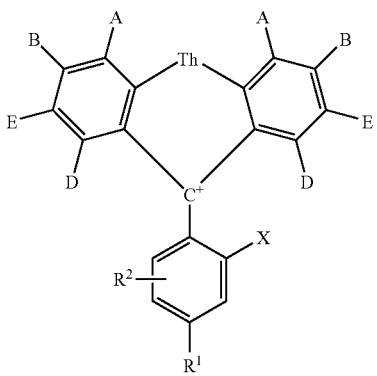

V wherein Th is O or S; $R^1$ is selected from the group consisting of H, $NR^3_2$, $OR^4$, alkyl, aryl and substituted aryl; $R^2$ is selected from the group consisting of H, $SO_3H$, $SO_3^-(1/n)$ $M^{n+}$, $CO_2H$ and $CO_2$-$(1/n)M^{n+}$; and each of A, B, E and D is independently selected from the group consisting of H, OH, $OR^4$, $NR^3_2$, F, Cl, Br, I, $NO_2$, CN, $^-NCS$ and $^-SCN$.

The present invention also provides a cyanine compound having the following chemical formula VI:

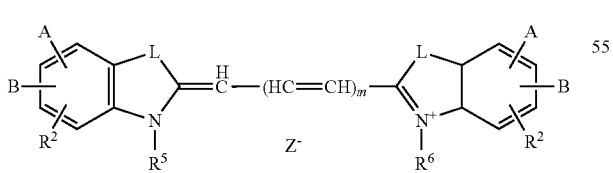

VI wherein L is selected from the group consisting of O, S and N—$R^7$; A and B is independently selected from the group consisting of H, OH, $OR^4$, $NR^3_2$, F, Cl, Br, I, $NO_2$, CN, $^-NCS$ and $^-SCN$; $R^2$ is selected from the group consisting of H, $SO_3H$, $SO_3^-(1/n)M^{n+}$, $CO_2H$ and $CO_2$-$(1/n)M^{n+}$; m is integer from 0 to 3; Z is selected from the group consisting of halide, tosylate, brosylate, carboxy-late, sulphate and phosphate; and each of $R^5$, $R^6$, $R^7$ is independently selected from the group consisting of alkyl, carboxyalkyl, alkylsulfonate, alkylaryl and polyalkylene oxide.

The present invention further provides a diazopyrrole compound having the following chemical formula VII:

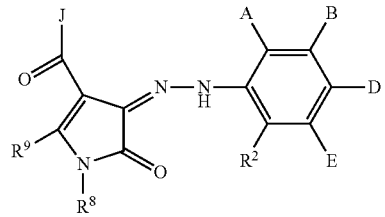

VII wherein each of A, B, E and D is independently selected from the group consisting of H, OH, $OR^4$, $N(R^3)_2$, F, Cl, Br, I, $NO_2$, CN, —NCS, —SCN and substituted aryl; $R^2$ is selected from the group consisting of H, $SO_3H$, $SO_3^-$ $(1/n)M^{n+}$, $CO_2H$ and $CO_2$-$(1/n)M^{n+}$; each of $R^3$ and $R^4$ is independently selected from the group consisting of alkyl, aralkyl, alkaryl and polyalkylene oxide; $R^8$ is selected from the group consisting of H, alkyl, aryl, substituted aryl, aralkyl, alkaryl and imidino; $R^9$ is selected from the group consisting of H, alkyl, $^-N(R^3)_2$, $^-OR^4$, aryl and substituted aryl; and J is NH-polyalkyene oxide or O-polyalkylene oxide.

Preferably, the diazopyrrole compound of chemical formula VII has the following chemical formula XXV:

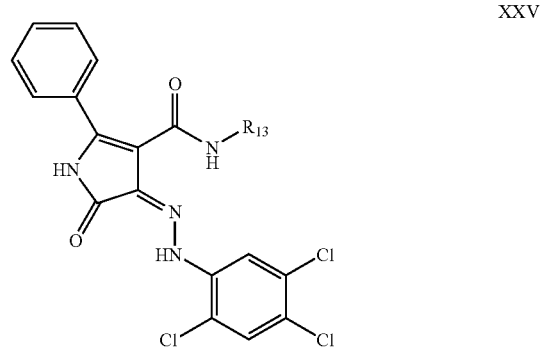

XXV wherein $R^{13}$ comprises $(C_aH_{2a}O)_m(C_bH_{2b}O)_nOCH_3$, where a and b are different and either 2 or 3, m is at least 3, and n is 1-31.

The present invention also provides a phthalocyanine compound having the following chemical formula IX:

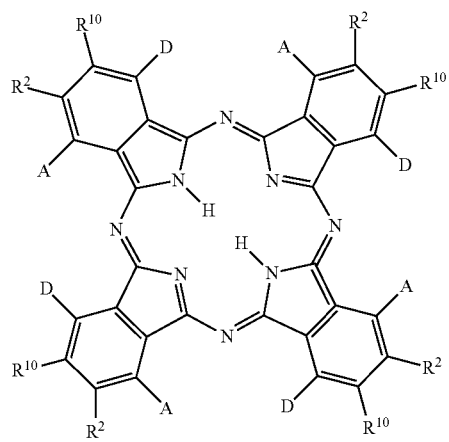

IX wherein each of A and D is independently selected from the group consisting of H, OH, OR$^4$, N(R$^3$)$_2$, F, Cl, Br, I, NO$_2$, CN, $^-$NCS and $^-$SCN; R$^2$ is selected from the group consisting of H, SO$_3$H, SO$_3^-$(1/n)M$^{n+}$, CO$_2$H and CO$_2$-(1/n)M$^{n+}$; and R$^{10}$ is selected from the group consisting of R$^2$, A, N(R$^3$)$_2$, OR$^4$ and SR$^4$.

The present invention further provides a phthalocyanine compound having the following chemical formula X:

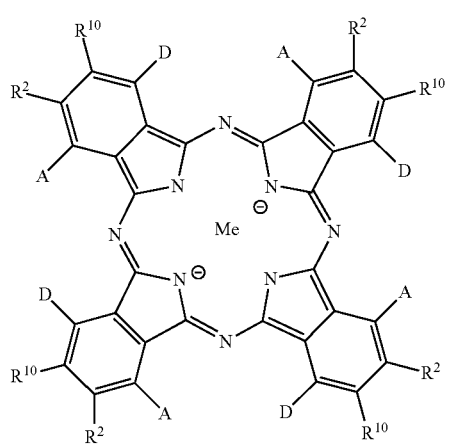

X wherein Me is MX$_n$(O)$_p^{2+}$, M is a cation derived from a metallic or semimetallic element, X is a halide or alkoxide, O is an oxygen atom, n is an integer from 0 to 3, and p is an integer from 0 to 1, each of A and D is independently selected from the group consisting of H, OH, OR$^4$, N(R$^3$)$_2$, F, Cl, Br, I, NO$_2$, CN, $^-$NCS and $^-$SCN; R$^2$ is selected from the group consisting of H, SO$_3$H, SO$_3^-$(1/n)M$^{n+}$, CO$_2$H and CO$_2$-(1/n)M$^{n+}$; and R$^{10}$ is selected from the group consisting of R$^2$, A, N(R$^3$)$_2$, OR$^4$ and SR$^4$.

The present invention also provides a naphthalocyanine compound having the following chemical formula XI:

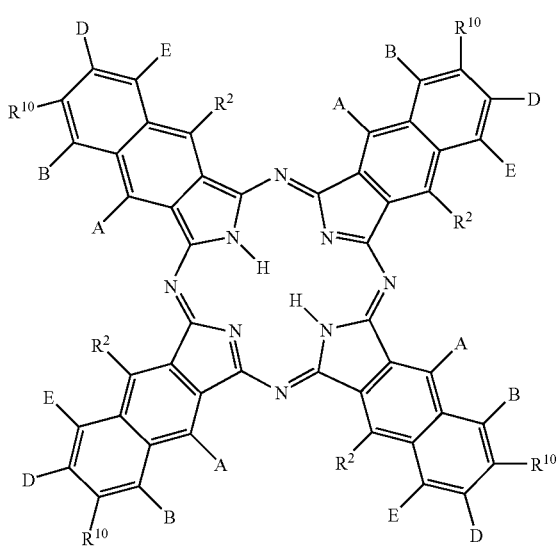

XI wherein each of A, D and E is independently selected from the group consisting of H, OH, OR$^4$, NR$^3_2$, F, Cl, Br, I, NO$_2$, CN, $^-$NCS and $^-$SCN; R$^2$ is selected from the group consisting of H, SO$_3$H, SO$_3^-$(1/n)M$^{n+}$, CO$_2$H and CO$_2$-(1/n)M$^{n+}$; and R$^{10}$ is selected from the group consisting of R$^2$, A, N(R$^3$)$_2$, OR$^4$ and SR$^4$.

The present invention further provides a naphthalocyanine compound having the following chemical formula XII:

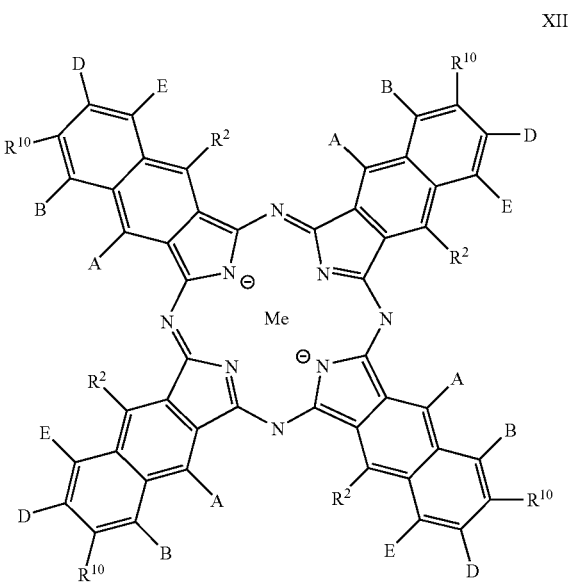

XII wherein Me is MX$_n$(O)$_p^{2+}$, M is a cation derived from a metallic or semimetallic element, X is a halide or alkoxide, O is an oxygen atom, n is an integer from 0 to 3, and p is an integer from 0 to 1, each of A, D and E is independently H, OH, OR$^4$, NR$^3_2$, F, Cl, Br, I, NO$_2$, CN, $^-$NCS and $^-$SCN; R$^2$ is selected from the group consisting of H, SO$_3$H, SO$_3^-$(1/n)M$^{n+}$, CO$_2$H and CO$_2$-(1/n)M$^{n+}$; and R$^{10}$ is selected from the group consisting of R$^2$, A, N(R$^3$)$_2$, OR$^4$ and SR$^4$.

The present invention also provides a coumarin or a carbostyril compound having the following chemical formula XIII:

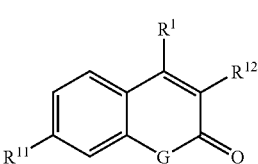

XIII wherein R$^1$ is selected from the group consisting of H, N(R$^3$)$_2$, OR$^4$, alkyl, aryl and substituted aryl; R$^{11}$ is selected from the group consisting of: N(R$^3$)$_2$,

XIV

-continued

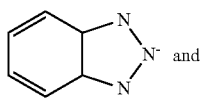
XV

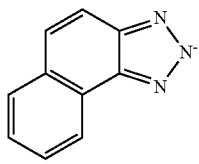
XVI $R^{12}$ is or A; G is O or $NR^5$; $R^5$ is independently selected from the group consisting of alkyl, carboxyalkyl, alkylsulfonate, alkylaryl and polyalkylene oxide; and A is selected from the group consisting of H, OH, $OR^4$, $NR^3_2$, F, Cl, Br, I, $NO_2$, CN, $^-NCS$ and $^-SCN$.

The present invention further provides a dialkyl succinosuccinate (DMSS) compound having the following chemical formula XVII:

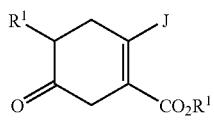
XVII wherein $R^1$ is selected from the group consisting of H, $NR^3_2$, $OR^4$, alkyl, aryl and substituted aryl; and J is NH-polyalkyene oxide or O-polyalkylene oxide.

Preferably, the dialkyl succinosuccinate (DMSS) compound of chemical formula XVII has the following formula XXVI:

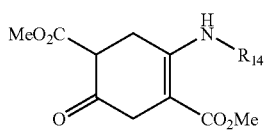
XXVI wherein $R^{14}$ comprises $(C_aH_{2a}O)_m(C_bH_{2b}O)_nCH_3$, where a and b are different and either 2 or 3, m is at least 3, and n is 1-31.

The present invention also provides a naphthaloperylene compound having the following chemical formula XIX:

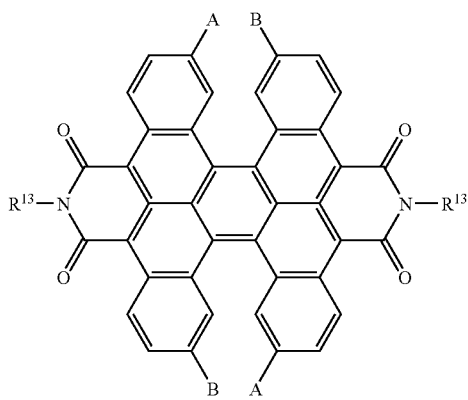
XIX wherein each of A and B is independently H, OH, $OR^4$, $NR^3_2$, F, Cl, Br, I, $NO_2$, CN, $^-NCS$ and $^-SCN$; and $R^{13}$ is polyalkylene oxide.

The present invention further provides a Lanthanide compound having the following chemical formula XX:

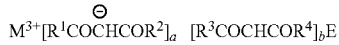
XX wherein M is a lanthanide; each of R1, R2 and R3 is independently selected from the group consisting of alkyl, alkaryl, aralkyl, cyano, haloalkyl, haloaryl, aryl, carboxy aryl, aryl sulfonate, heterocyclic and $R^4$; $R^4$ is selected from the group consisting of —NH [polyalkylene oxide], —O [polyalkylene oxide], and

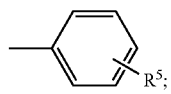
XXI $R^5$ is selected from the group consisting of —CONH [polyalkylene oxide], —$CO_2$ [polyalkylene oxide], —$SO_3$ [polyalkylene oxide] and —$SO_2NO$ [polyalkylene oxide]; a is an integer from 0-2; b is an integer from 1-3; and E is

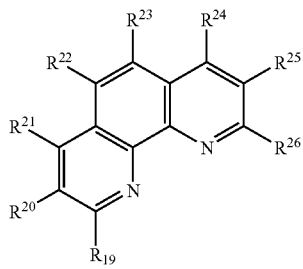
XXII where R19 through R26 are each independently H, alkyl, alkoxy, halide, sulfonic acid.

The present invention also provides a Lanthanide compound having the following chemical formula XXIII:

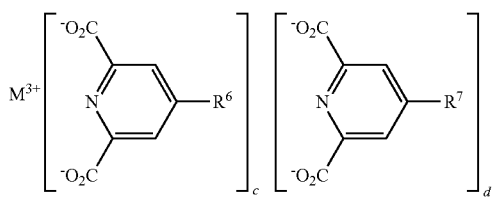
XXIII wherein M is a lanthanide; c is an integer from 0-2; d is an integer from 1-3; $R^6$ is selected from the group consisting of H, alkyl, alkaryl, sulphonic acid, carboxylic acid, halide, alkoxy, sulphonamide, carboxamide and $R^7$; and $R^7$ is selected from the group consisting of CONH [polyalkylene oxide], $CO_2$ [polyalkylene oxide], $SO_2NH$ [polyalkylene oxide] and $SO_3$ [polyalkylene oxide].

The present invention further provides a method of tagging an article with a fluorescent taggant comprising coating said article with a coating composition containing a compound having the following chemical formula XXIV:

$$K-T_w \quad \quad XXIV$$

wherein K is a fluorescent moiety; T is a pendant group comprising a polyalkylene oxide residue; and w is a number greater than zero.

Other objects and advantages of the present invention will become apparent from the following description and appended claims.

DETAILED DESCRIPTION OF THE INVENTION

Figure 1:
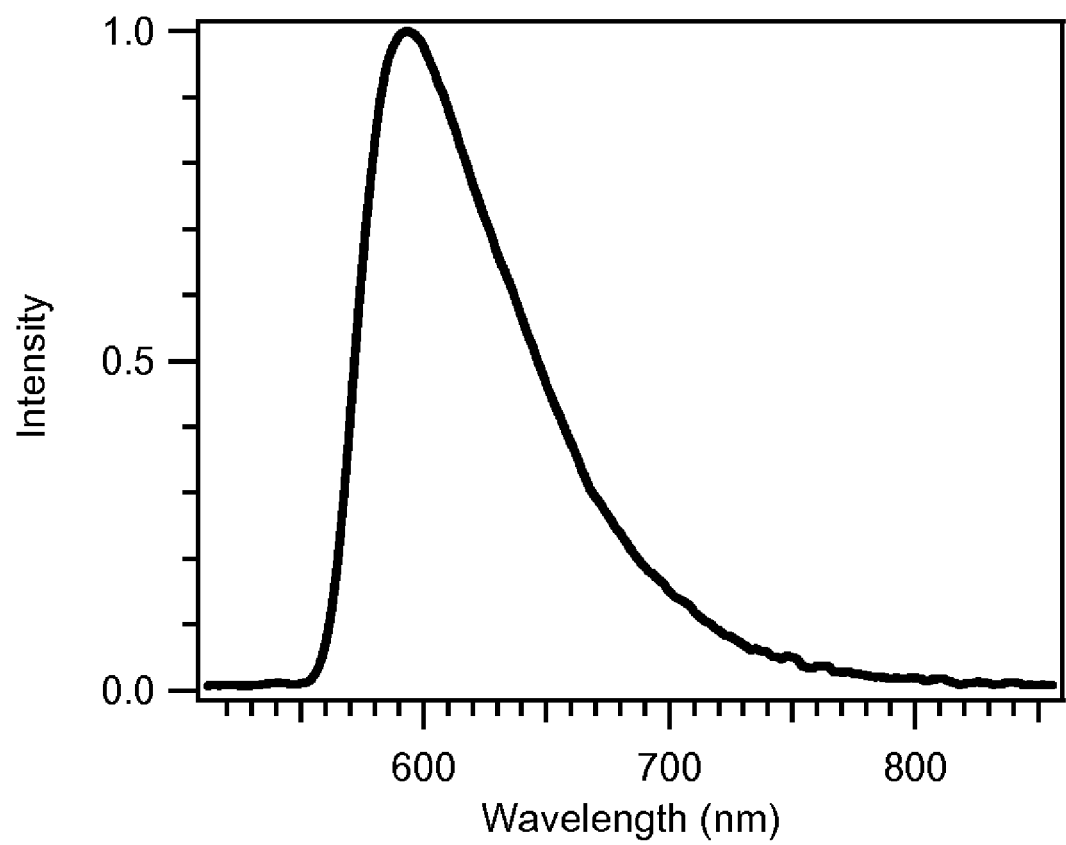
FIG. 1 shows the spectrum for a printed sample of ink Formulation #1.

It has now been demonstrated that substituents such as poly(oxyalkylene) attached to pigment molecules or fluorescent compounds exhibit high fluorescence in ink formulations and are readily soluble in organic solvents are high concentrations. Accordingly, solutions of these materials, i.e. compounds of the present invention, exhibit high fluorescence in ink formulations such that they are useful for security taggant applications.

The pigment or fluorescent compounds used in preparing the compounds of the present invention include but are not limited to the group consisting of perylene, xanthene, thioxanthene, cyanine, diazopyrrole, phthalocyanine, naphthalocyanine, coumarin, carbostyril, dialkylsuccinosuccinate, naphthaloperylene and derivatives thereof.

The terms "coating composition" and "security applications" for the purpose of the present invention mean a composition to be applied to an underlying substrate of an article where such application is used to subsequently recognize such article.

Compounds of the present invention may be prepared by having substituents such as poly(oxyalkylene) attached via a nitrogen or oxygen moiety to a functional residue in the fluorescent colorant molecule. Examples of this, for the class of peylene colorants described in this invention, include either the imide nitrogen of perylene bisimides or the amide nitrogen of perylene tetraamides. These substituents are much more efficient at solubilizing a perylene molecule. These perylene poly(oxyalkylene) bisimides and tetraamides are readily soluble in common organic solvents in high concentrations. For other colorant types, the poly(alkylene oxide) moiety may be attached via an imide (for example, in dialkylsuccinosuccinate dyes) or an amide (for example, in azopyrrole dyes), as an ester, or as a sulfonamide, or via other functional residues known to those skilled in the art.

Perylene poly(oxyalkylene)bisimides are prepared by reacting purified perylene tetracarboxylic acid dianhydride with poly(oxyalkylene)amines, which are readily available from Huntsman Corp. The reaction is performed in a polar aprotic solvent such as n-methylpyrrolidinone with or without the presence of a Lewis acid catalyst such as zinc acetate dihydrate at a temperature preferably between 100-210° C., most preferably between 150-200° C.

Perylene poly(oxyalkylene)tetraamides are prepared in a two step process. The first step is reaction between a secondary amine and purified perylene tetracarboxylic acid dianhydride, giving a perylene bisamide, biscarboxylic acid. Preferred conditions are to perform this reaction in a polar solvent such an alcohol or water, most preferably water at a temperature between ambient to 100° C., most preferably 50° C. The second step is to react the perylene bisamide, biscarboxylic acid with a poly(oxyalkylene)amine. The reaction is performed in a polar aprotic solvent such as n-methylpyrrolidinone with or without the presence of a Lewis acid catalyst such as zinc acetate dihydrate at a temperature preferably between 100-210° C., most preferably between 150-200° C.

Compounds of the present invention, preferably, Perlyene poly(oxyalkylene)bisimides and Perlyene poly(oxyalkylene) tetra amides exhibit excellent light fastness for indoor applications. The excellent solubility of these materials in common ink vehicles allows for stable ink formulations that can be used in demanding applications such as in water-based ink jet inks, solvent-based ink jet inks, flexo inks, energy curable inks and Offset inks. The high fluorescence, light fastness and good solubility make these ideal fluorescent security taggants that can be formulated into jettable ink. Preferably, the compounds of the present invention are present in an amount from about 0.01 to about 20%, more preferably from about 0.1 to about 10% by weight of an ink or coating composition.

EXAMPLE 1

A Perylene Poly(oxyalkylene)Bisimide Compound (Compound B)

In a 2000 ml 4-necked flask was dispersed 100.0 g 3,4,9, 10-perylene tetracarboxylic acid dianhydride, 306.0 g of methoxypoly(oxyethylene/oxypropylene)-2-propylamine (MW=600), 11.19 g zinc acetate dihydrate and 1000 ml n-methylpyrrolidinone. The mixture was heated to 200° C., allowing the evolved water to distill out of the flask. Held at 200° C. for 15 hours, then cooled to room temperature and drowned into 10 liters water. The product was collected by filtration and washed with water until no n-methylpyrrolidinone was detected in the filtrate. The wet presscake was slurried into 6000 ml 5% aqueous sodium hydroxide and stirred at 80° C. for 1 hour, filtered and washed with water until the pH and conductivity of the filtrate was equivalent to that of the wash water, dried in an oven at 80° C. Perylene poly(oxyalkylene)bisimide (342.35 g; 86%) was isolated as a red rubbery solid. The product exhibited good solubility in common organic solvents such as acetone and methanol. In addition, it exhibited a significant fluorescence emission maximum near 553 nm when excited at 365 nm, 470 nm or 500 nm. When formulated into an ink-jet ink, printed on paper and exposed to visible or UV light, it showed excellent fluorescence.

EXAMPLE 2

Preparation of a Perylene Poly(oxyalkylene)Tetraamide Compound

In a 2000 ml 4-necked flask, 3,4,9,10-perylene tetracarboxylic acid dianhydride presscake (150.0 g based on dry color) was dispersed into 1400 ml water. Diethylamine (112.05 g) was added and heated to 50° C. and held for 3 hours, then cooled. The mixture was acidified with concentrated hydrochloric acid until the slurry did not bleed when spotted on filter paper. The product was filtered and washed with water until the pH and conductivity of the filtrate was equivalent to that of the wash water. Perylene bis diethylamide bis carboxylic acid presscake (610.55 g) was isolated with a moisture content of 27.58% (168.39 g dry, 82% yield).

In a 500 ml 4-necked flask, perylene bis diethylamide bis carboxylic acid presscake (10.0 g based on dry color) was dispersed into 100 ml n-methylpyrrolidinone. Methoxypoly(oxyethylene/oxypropylene)-2-propylamine (22.32 g; MW=600) was added and heated to 200° C., allowing the evolved water to distill out of the flask. The temperature was held at 200° C. for 15 hours, then cooled to room temperature and drown into 1000 ml water. The product was collected by filtration and washed with water until no n-methylpyrrolidinone was detected in the filtrate. The collected product was then dried in an oven at 80° C. The isolated product (23.3 g; 74%) was a mixture of perylene bis diethylamide bis poly(oxyalkylene)amides as a red rubbery solid. The product exhibited good solubility in common organic solvents such as acetone and methanol. In addition, it exhibited a significant fluorescence emission maximum near 526 nm when excited at 365 nm, 470 nm or 500 nm. When formulated into an ink-jet ink, printed on paper and exposed to visible or UV light, it showed excellent fluorescence.

EXAMPLE 3

Preparation of a Perylene Poly(oxyalkylene)Bisimide Compound

Scheme I

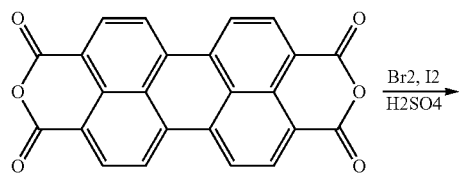

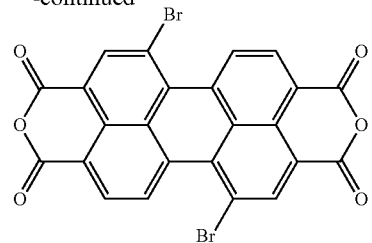

As outlined in scheme I above (described in German Patent DE 195 47 209 A1), the starting material (14.6 g, 37.2 mmol) was suspended in concentrated Sulfuric acid (221 g) and stirred overnight at room temperature. To the suspension was added I2 (350 mg, 1.38 mmol), and the mixture heated to 85° C. Bromine (4.22 ml, 82.6 mmol) was added dropwise over ~30 min. The mixture was allowed to stir for 20 hours at 85° C. After cooling, the excess bromine was removed by a stream of nitrogen. Water (35 ml) was added dropwise to the reaction mixture, and the suspension heated to 85° C. for one hour. After cooling, the reaction mixture was filtered (M porosity glass frit) and washed repeatedly with water until the filtrate registered neutral to litmus. The red solid thus obtained was dried at 65-70 C for 4 days. The yield was a red powder (18.75 g).

Scheme II

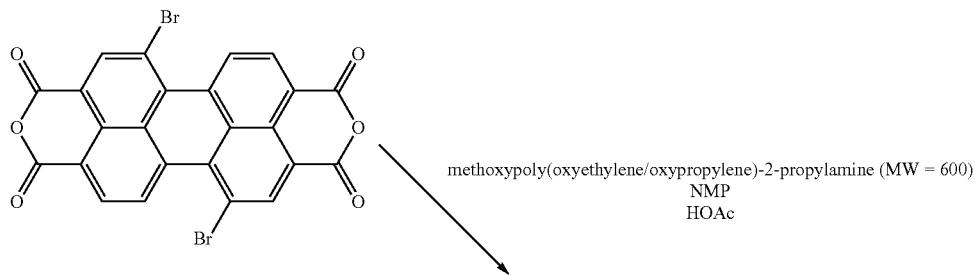

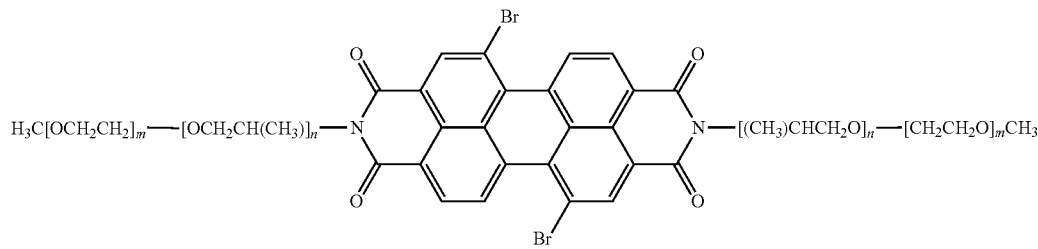

wherein *m* is at least 3 and *n* is 1-31 and the ratio of *m* to *n* is from 1 to 9.

The dibromoperylene (5.0 g, 9.1 mmol) was suspended in 55 ml N-methylpyrollidone containing 250 µl of acetic acid, and heated to 95° C. (bath temp). The methoxypoly(oxyethylene/oxypropylene)-2-propylamine (11 g, ~18.5 mmol; MW=600) was added in portions over 2 hours. Continued heating at 95 C over the next 7 hours, during which time the reaction mixture gradually became homogenous. After stirring overnight at room temperature, the mixture was poured into 500 ml of water. An immediate tarry red material separated, which was isolated by decanting the supernatant liquid after standing for 1 hour. This reaction is described in Scheme II above. The tarry solid was dissolved in $CH_2Cl_2$, dried over $Na_2SO_4$, filtered and evaporated to yield approximately 11 g of a viscous red oil.

EXAMPLE 4

Preparation of a DMSS Compound (Compound C)

Dimethyl 2,5-dioxo-1,4-cyclohexane dicarboxylate (8.94 g; 0.0392 mol) was dispersed into methoxypoly(oxyethylene/oxypropylene)-2-propylamine (80 g; 0.0392 mol; MW=2000) in a 500 ml 4-necked flask. Five drops of concentrated hydrochloric acid was added to the dispersion which was then heated to 120° C. while passing a slow stream of nitrogen over the reaction mixture. Water was then distilled out of the flask during the heat-up period and while at 120° C. After 2.5 hours, residual water was removed under vacuum.

Scheme III

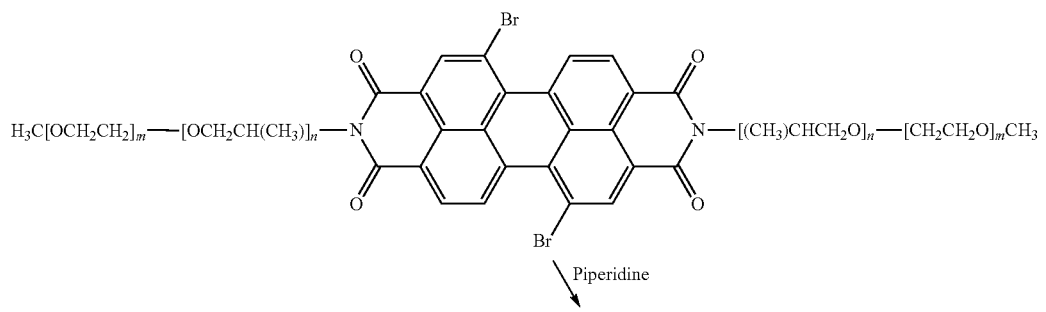

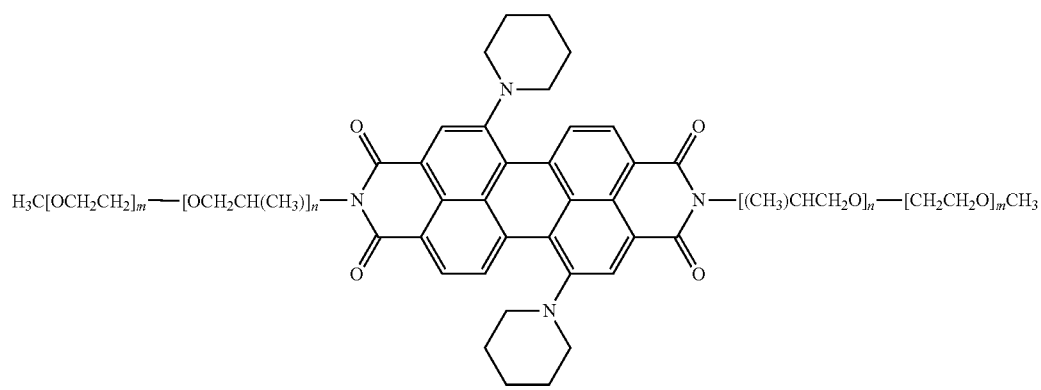

wherein m is at least 3 and n is 1-31 and the ratio of m to n is from 1 to 9.

The dibromo compound (about 5 g) was added to piperidine (35 ml) and heated to 75° C. under $N_2$ for 16 hours as indicated in Scheme III above. After cooling to room temperature, the mixture was evaporated, then evaporated again from toluene. The residue was eluted over silica with a gradient of $CH_2Cl_2$, followed by 1%, 2%, 3%, 4% EtOH in $CH_2Cl_2$ containing 0.2% Et3N. A blue-green band elutes first which appears as one spot on TLC. The yield was 1.9 g of a blue-green oil, highly fluorescent, with an Emission max of 765 nm and an Excitation max of 693 nm in ethanol.

Similarly, pyrrolidine can be substituted for piperidine in the final reaction step to yield the bis-pyrrolidinyl product.

The cooled product shown below in chemical formula XVIII was isolated as an amber oil was soluble in common solvents such as acetone and exhibited fluorescent characteristics.

XVIII

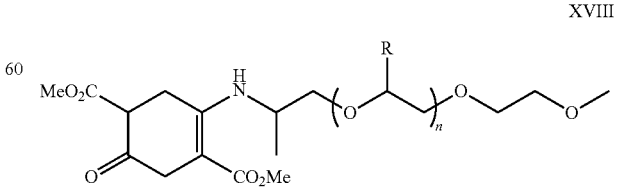

wherein R is 95% $CH_3$ and 5% H and n is about 35.

The final product of the DMSS compound (Compound C; about 1 mg) was dissolved separately into each of methanol (100 ml MeOH) and methyl ethyl ketone (100 ml MEK). The fluorescence was taken at excitation of 470 nm, excitation slit of 15.0 nm, emission slit of 15.0 nm with measurements from 200-900 nm@250 nm/minute. It was also determined that there was an excitation maximum at 345 nm so a second emission was determined using the same conditions but with an excitation wavelength of 345 nm. The fluorescence measurements are described in Table 1 below.

TABLE 1

| Sample | @ 345 nm excitation | | @ 470 nm excitation | |
|---|---|---|---|---|
| | Max Wavelength | Intensity | Max Wavelength | Intensity |
| Compound C in MEK | 441.08 | 360.24 | 520.55 | 257.45 |
| Compound C in MeOH | 445.25 | 365.54 | 524.04 | 119.02 |
| MEK Blank | | | 528.43 | 16.70 |
| MeOH Blank | 432.15 | 18.08 | | |

It is clear from the results shown above the Compound C has a significant fluorescence when excited at 345 nm and 470 nm.

EXAMPLE 5

Preparation of an Azopyrrole Compound (Compound A)

2-Phenyl-3-ethoxycarbonyl-4-(2,4,5-trichlorophenylhydrazonyl)-1H-5-pyrrolinone (4.00 g; 0.00912 mol) made analogously as described in Example 7 of U.S. Pat. No. 6,965,019 was mixed with methoxypoly(oxyethylene/oxypropylene)-2-propylamine (5.47 g; 0.00912 mol; MW=600) and 1-methyl-2-pyrrolinidinone (NMP; 1 ml) in a 250 ml 4-necked flask. The mixture was heated to 200° C. and held for 3.5 hours, at which time the NMP was removed under reduced pressure. The product was isolated upon cooling as a dark oil which dissolved into common solvents such as acetone and exhibited fluorescent characteristics. The product has the following chemical formula VIII:

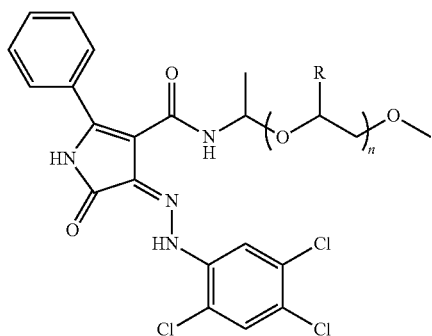

VIII wherein R is 90% CH3 and 10% H and n an integer from about 9 to 10.

The final product of the azopyrrole compound (Compound A; about 1 mg) was dissolved separately into each of methanol (100 ml MeOH) and methyl ethyl ketone (100 ml MEK). The fluorescence was taken at excitation of 470 nm, excitation slit of 15.0 nm, emission slit of 15.0 nm with measurements from 200-900 nm@250 nm/minute. It was also determined that there was an excitation maximum at 345 nm so a second emission was determined using the same conditions but with an excitation wavelength of 345 nm. For a drawdown of the azopyrrole compound, a piece was cut and run using the paper attachment for the Fluorescence Spectrophotomoter using the previous conditions at 470 nm. A blank paper was run as well along with blanks of MEK and MeOH at each excitation. The fluorescence measurements are described in Table 2 below.

TABLE 2

| Sample | @ 345 nm excitation | | @ 470 nm excitation | |
|---|---|---|---|---|
| | Max Wavelength | Intensity | Max Wavelength | Intensity |
| Compound A in MEK | 428.96 | 956.59 | 524.3 | 147.73 |
| Compound A in MeOH | 424.97 | 158.4 | 525.03 | 112.06 |
| Compound A Drawdown | | | 526.17 | 111.52 |
| MEK Blank | | | 528.43 | 16.70 |
| MeOH Blank | 432.15 | 18.08 | | |
| Drawdown Blank | | | 520.46 | 57.13 |

It is clear from the results shown above the Compound A has a significant fluorescence when excited at 345 nm and 470 nm. However, Compound A has much stronger fluorescence emission when excited at 345 nm.

EXAMPLE 6

Preparation of Ink Formulation #1 Containing the Azopyrrole Compound Prepared in Example 5

A continuous inkjet (CIJ) ink was prepared by using the material listed in Table 3 below. First, the Azopyrrole compound prepared in Example 5 (Compound A) was added to half of the total MEK (methylethylketone) volume followed by stirring until a solution was obtained. Subsequently the resin VMCC (Dow Chemical) was introduced into the mixture followed by further mixing to obtain a solution, followed by the addition of potassium thiocyanate and more mixing. A second solution was obtained by addition of the black colorant Microlith CK (Ciba) to the remainder of the MEK solvent and mixing by a high shear mixer at 10000 rpm for 40 minutes. The two mixtures were then combined, mixed and filtered through a 1 micron filter to obtain the finished ink.

TABLE 3

| Components | % w/w |
|---|---|
| MEK | 90.7 |
| Microlith CK | 0.5 |
| Compound A | 1.8 |
| Resin VMCC | 6.3 |
| KSCN | 0.7 |

The viscosity and conductivity of this ink were measured by standard methods and they were determined to be within the acceptable range as recommended for typical CIJ printers. Test printing was carried out using a Videojet Excel 2000 CIJ printer on a variety of substrates. The luminescence of printed samples were characterized by using an Ocean Optic H4000 spectrometer using a bifurcated probe, a halogen light source or a 488 nm Argon laser and appropriate optical filters. For solution samples, a Cary Eclipse spectrometer was used and a triangular cell for front face emission was utilized. The spectral information for a number of samples is indicated in Table 4. FIG. 1 provides the spectrum for a printed sample of ink Formulation #1.

TABLE 4

| Material | Emission peak (nm) |
| --- | --- |
| Ink Formulation #1 | 543 |
| Ink Formulation #2 (see Example 7 below) | 570 |
| Ink Formulation #3 (see Example 8 below) | 574 |

EXAMPLE 7

Preparation of Ink Formulation #3 Containing the Perylene Poly(oxyalkelene) Compound Prepared in Example 1

An additional CIJ ink was prepared by using the perylene poly(oxyalkelene) compound prepared in Example 1 (compound B) in a process similar to that of Example 6 based on the material indicated in Table 5.

TABLE 5

| Components | % w/w |
| --- | --- |
| MEK | 88.5 |
| Microlith CK | 3.6 |
| Compound B | 0.9 |
| Resin VMCC | 6.3 |
| KSCN | 0.7 |

EXAMPLE 8

Preparation of Ink Formulation #2 Containing the DMSS Compound Prepared in Example 4

A different CIJ ink was prepared by using the DMSS compound prepared in Example 4 (Compound C) in a process similar to that of Examples 6 and 7 based on the material indicated in Table 4.

TABLE 4

| Components | % w/w |
| --- | --- |
| MEK | 90.7 |
| Microlith CK | 0.5 |
| Compound C | 1.8 |

TABLE 4-continued

| Components | % w/w |
| --- | --- |
| Resin VMCC | 6.3 |
| KSCN | 0.7 |

The invention has been described in terms of preferred embodiments thereof, but is more broadly applicable as will be understood by those skilled in the art. The scope of the invention is only limited by the following claims.

What is claimed is:

1. A perylene poly(oxyalkylene) bisimide compound having the following chemical formula I:

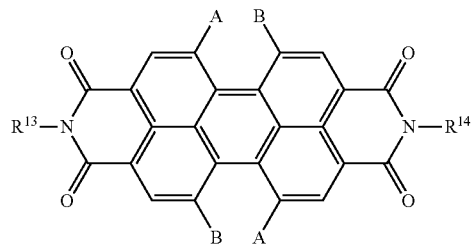

wherein each of A and B is independently selected from the group consisting of: H, OH, $OR^4$, $N(R^3)_2$, alkyl, F, Cl, Br, I, $NO_2$, CN, $^-NCS$, $^-SCN$; $R^3$ is selected from the group consisting of: alkyl, aralkyl, alkaryl, polyalkylene oxide; and each of $R^{13}$ and $R^{14}$ is independently a polyalkylene oxide.

2. The perylene compound of claim 1, wherein each of A and B is H; and each of $R^{13}$ and $R^{14}$ comprises $(C_aH_{2a}O)_m(C_bH_{2b}O)_nCH_3$, where a and b are different and either 2 or 3, m is at least 3, and n is 1-31.

3. An ink or a coating composition comprising the perylene compound of claim 1.

4. The composition of claim 3, wherein said compound is present in an amount from about 0.01 to about 20% by weight.

5. The composition of claim 3 being a water-based ink jet ink.

6. The composition of claim 3 being a solvent based ink jet ink.

7. The composition of claim 3 being a flexo ink.

8. The composition of claim 3 being an energy curable ink.

9. The composition of claim 3 being an offset ink.

10. The composition of claim 3 being a coating composition for security applications.

11. An article coated with the composition of claim 3.

12. A method of tagging an article with a fluorescent taggant comprising coating said article with the coating composition of claim 3.

* * * * *